United States Patent [19]
Saito et al.

[11] Patent Number: 5,803,929
[45] Date of Patent: Sep. 8, 1998

[54] ULTRAVIOLET ABSORBER CONTAINING A BENZOTRIAZOLE COMPOUND

[75] Inventors: Hajime Saito; Masahiro Makino, both of Sabae, Japan

[73] Assignee: Nicca Chemical Co., Ltd., Fukui, Japan

[21] Appl. No.: 821,717

[22] Filed: Mar. 20, 1997

Related U.S. Application Data

[62] Division of Ser. No. 591,791, Jan. 25, 1996, abandoned.

[30] Foreign Application Priority Data

Sep. 29, 1995 [JP] Japan .................................. 7-253276

[51] Int. Cl.⁶ .............................. D06P 1/642; D06P 5/06; D06M 13/352
[52] U.S. Cl. ..................... 8/115.58; 8/115.6; 8/115.65; 8/490; 252/8.61; 252/589; 548/260; 430/512
[58] Field of Search ............................... 8/115.58, 115.6, 8/115.65, 490; 252/8.61, 589; 548/260; 430/512

[56] References Cited

U.S. PATENT DOCUMENTS

| | | | |
|---|---|---|---|
| 3,213,058 | 10/1965 | Boyle et al. | 528/96 |
| 3,214,436 | 10/1965 | Boyle | 260/308 |
| 3,383,241 | 5/1968 | Davisson, Sr. | 117/138.8 |
| 3,766,205 | 10/1973 | Heller et al. | 548/260 |
| 4,486,518 | 12/1984 | Kesselman et al. | 430/5 |
| 4,668,235 | 5/1987 | Evans et al. | 8/115.58 |
| 4,990,623 | 2/1991 | Berenbaum et al. | 548/260 |
| 5,455,152 | 10/1995 | Vishwakarma | 430/512 |
| 5,516,436 | 5/1996 | Uchida et al. | 252/8.6 |

FOREIGN PATENT DOCUMENTS

| | | |
|---|---|---|
| 0704754 A3 | 4/1996 | European Pat. Off. |
| 0717313 A1 | 6/1996 | European Pat. Off. |
| 2505309 A1 | 8/1975 | Germany . |
| 49-61069 | 6/1974 | Japan . |
| 50-120486 | 9/1975 | Japan . |
| 60-59185 | 4/1985 | Japan . |
| 2-41468 | 2/1990 | Japan . |
| 4-91274 | 3/1992 | Japan . |
| 6-192972 | 7/1994 | Japan . |

*Primary Examiner*—Fiona T. Powers
*Assistant Examiner*—Laura L. Stockton
*Attorney, Agent, or Firm*—McAulay Fisher Nissen Goldberg & Kiel, LLP

[57] ABSTRACT

An ultraviolet absorber comprising, as an effective component, a benzotriazole compound represented by the following general formula (I)

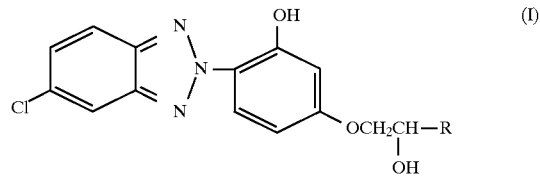

wherein R represents hydrogen, methyl, ethyl or phenyl. The ultraviolet absorber undergoes minimal sublimation, has excellent thermal resistance, provides satisfactory light fastness for materials made of polyester-based synthetic fibers, particularly cation-dyeable polyester-based fibers, and is also inexpensive, generates few by-products and is easy to produce industrially.

20 Claims, No Drawings

ULTRAVIOLET ABSORBER CONTAINING A BENZOTRIAZOLE COMPOUND

This application is a division of application Ser. No. 08/591,791, filed Jan. 25, 1996, now abandoned.

BACKGROUND OF THE INVENTION

1. Field of the Invention

The present invention relates to an ultraviolet absorber, and particularly to an ultraviolet absorber which is useful as a treating agent to improve the color fastness to light of materials made of polyester fibers, and other synthetic fibers, which undergo changes in color when exposed to light.

2. Description of the Related Art

Car seats, car mats, seat belts and the like, which require high durability and high color fastness to light and consist of materials made of polyester fibers and other synthetic fibers, are commonly treated with an ultraviolet absorber added to a dyeing bath or a printing paste.

Japanese Unexamined Patent Publications No. 60-59185 and No. 2-41468, for example, disclose fiber materials impregnated with 2-(2'-hydroxy-3'-t-butyl-5'-methylphenyl)-5-chlorobenzotriazole but, upon heating to 160°–190° C. in the post-dyeing thermal treatment (finish setting) step, sublimation occurs from the surface of the fibers, creating the problems of contamination of the finish setting machine and lower color fastness to light. As alternatives, Japanese Unexamined Patent Publication No. 4-91274 discloses 2-[2'-hydroxy-3'-(3",4",5",6"-tetraphthalimidomethyl)-5'-methylphenyl] benzotriazole and 2,2'-dihydroxy-4,4'-dimethoxybenzophenone, indicating that they are sublimation-resistant ultraviolet absorbers. The problems of the former, however, include the fact that it is inferior to conventional products in terms of its effect of preventing color changes due to light, and it undergoes whitening and yellowing by photodecomposition of the compound itself upon prolonged exposure to xenon light sources which are said to have a wavelength near that of sunlight. On the other hand, the problems of the latter compound include the fact that the deep yellow color of the compound itself leads to changes in color when used to treat light colors.

In addition, Japanese Unexamined Patent Publication No. 6-192972 discloses 1,4-bis-(4-benzoyl-3-oxyphenoxy)butane, and recently 2-(2'-hydroxy-4'-methoxyphenyl)-4,6-diphenyl-s-triazine has become known, both of which have excellent resistance to sublimation, and are useful for improving the color fastness to light of dyed polyester-based fibers with high-temperature treatment; nevertheless, these compounds do not adsorb well onto materials made of cation-dyeable polyester-based fibers, which have been used in recent years in car seats and the like, and thus do not exhibit an effect of improving the color fastness to light of such fibers.

In addition, although Japanese Unexamined Patent Publication No. 49-61069 discloses an epoxy-addition reaction to 2-(2',4'-dihydroxyphenyl)benzotriazoles, it contains no concrete description regarding the properties or performance of compounds according to the present invention.

SUMMARY OF THE INVENTION

In light of the prior art described above, it is an object of the present invention to provide an ultraviolet absorber which undergoes minimal sublimation, has excellent thermal resistance, provides satisfactory light fastness for materials made of polyester-based synthetic fibers, particularly cation-dyeable polyester-based fibers, and which is also inexpensive, generates few by-products and is easy to produce industrially.

In order to achieve this object, the present invention provides an ultraviolet absorber comprising as an effective component a benzotriazole compound represented by the following general formula (I)

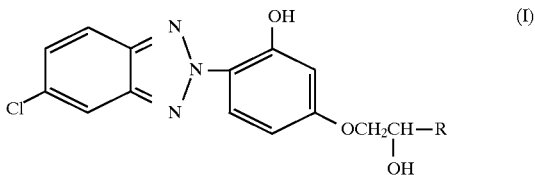

wherein R represents hydrogen, methyl, ethyl or phenyl.

The present inventors have completed the present invention on the basis of the finding that improved color fastness to light may be imparted to a fiber material by adsorbing at least one type of the general compound indicated above onto the fiber material in an amount usually of 0.01–10%, and preferably 0.1–5%, with respect to the fiber weight, and that these compounds, having excellent resistance to sublimation, do not result in contamination of finish setting machines or lower light fastness even after the thermal treatment process, and furthermore that they adsorb well onto cation-dyeable polyester-based fiber materials and are thus very useful as ultraviolet absorbers for the treatment of fibers.

DESCRIPTION OF THE PREFERRED EMBODIMENTS

Fiber materials which may be effectively treated with the ultraviolet absorber of the invention include fabrics and knits made of polyester-based synthetic fibers or composite materials comprising both polyester-based synthetic fibers and cotton, rayon, wool, nylon, acetate or other fibers, as well as carpets, car seats, car mats, seat belts and the like made of the corresponding raised fabrics. Any of a variety of methods including continuous treatment by padding with an aqueous dispersant, adsorption by immersion, printing, treatment with a solvent, etc. may be used to apply the above-mentioned ultraviolet absorber to the fiber material, and it is not necessarily limited to these methods. These treatments may be carried out either before or after the steps of dyeing or printing, or they may be carried out in the same treatment bath. Treatment in an aqueous system requires uniform dispersion in the water, which may be easily accomplished by a publicly known method such as fine crushing with a bead mill using an appropriate amount of an anionic surfactant and/or a nonionic surfactant.

The compound represented by the above-mentioned general formula (I) may be produced by an addition reaction of 2-(2',4'-dihydroxyphenyl)-5-chlorobenzotriazole represented by the following formula (II)

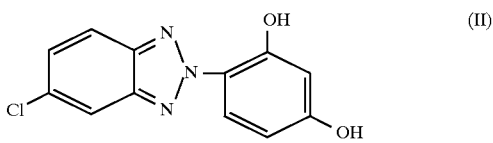

with an epoxy compound represented by the following general formula (III)

(III)

wherein R represents the same species as stated previously, the compound being ethylene oxide, propylene oxide, butylene oxide or styrene oxide.

Here, the epoxy compound represented by the general formula (III) is preferably used in an amount of 1.0 to 5.0 equivalents, and especially 1.0 to 2.0 equivalents, to one equivalent of the 2-(2',4'-dihydroxyphenyl)-5-chlorobenzotriazole represented by formula (II). If it is present in a lower amount, a large amount of the starting material remains after the reaction, while if it is present in too great an amount, it is added at 2 equivalents or more, making it impossible to obtain the desired ultraviolet absorbing property.

Commonly employed, publicly known processes may be used for the reaction, i.e. a pressure reaction with or without a solvent, using an alkali metal, alkaline earth metal, organometallic compound, Lewis acid, amine, quaternary ammonium salt, etc. as the catalyst. A solution process wherein the reaction is conducted in a solvent is especially suitable from the standpoint of ease of scaling-up, high reaction efficiency and minimal by-products. Solvents which may be used include aromatic hydrocarbon solvents such as benzene, toluene, xylene and mesitylene, alcoholic solvents such as methanol, ethanol, n-propanol, isopropanol, n-butanol, isobutanol, t-butanol, n-hexanol and cyclohexanol, and water/alcohol mixture solvents such as water/methanol, water/ethanol, water/n-propanol and water/isopropanol. Catalysts which may be used include sodium hydroxide, potassium hydroxide, calcium hydroxide, sodium acetate, calcium acetate, sodium methoxide, sodium ethoxide, t-butoxypotassium, methyllithium, butyllithium, triphenylphosphine, boron trifluoride, zinc chloride, aluminum chloride, triethylamine, pyridine, tetramethylammonium chloride, benzyltrimethylammonium chloride, etc., of which tetramethylammonium chloride is particularly suitable.

The reaction temperature is preferably between 50° C. and 150° C., and more suitably between 90° C. and 120° C.

The ultraviolet absorber of the present invention is synthesized by an addition reaction of an epoxide to 2-(2',4'-dihydroxyphenyl)-5-chlorobenzotriazole which is easily obtainable, and since the desired product is obtained in a roughly quantitative manner, industrial production thereof is possible. Furthermore, since the molecule contains an alcoholic hydroxyl group, it has excellent resistance to sublimation and stability at high temperatures. Its adsorbence is particularly high when it is crushed finely and impregnated into the polyester fibers, which then exhibit the same character as cation-dyeable polyester fibers, and thus the result is a very satisfactory improvement in the color fastness to light.

The ultraviolet absorber of the present invention may also contain a mixture of 2 or more compounds represented by the general formula (I). If necessary, it may also be used in combination with a conventional publicly known ultraviolet absorber, antioxidant, photostabilizer, or the like.

The present invention will now be explained in detail by way of the following examples.

The melting points given in these examples were determined based on the endothermic peaks obtained using a differential scanning calorimeter (hereunder abbreviated to DSC) manufactured by Shimazu Seisakusho. The nuclear magnetic resonance (hereunder abbreviated to NMR) spectra were measured using an FT-NMR R-1900 manufactured by Hitachi Seisakusho. The infrared absorption (hereunder abbreviated to IR) spectra were measured using a Perkin-Elmer 1650 manufactured by Perkin-Elmer. The thermal weight loss ratios were measured using a DTG-50 simultaneous differential thermal/thermogravimetric apparatus manufactured by Shimazu Seisakusho.

The compound represented by formula (I) may usually be obtained by diazotizing an o-nitroaniline by a common method, coupling it with resorcin by a common method to make an azo compound, reducing this to obtain 2-(2',4'-dihydroxyphenyl)-5-chlorobenzotriazole, and then adding an epoxy compound thereto by an addition reaction. A production process for this compound is described in detail below.

EXAMPLE 1

Into a 1000 ml autoclave were charged 400 g of isopropyl alcohol, 100 g of 2-(2',4'-dihydroxyphenyl)-5-chlorobenzotriazole, 0.5 g of tetramethylammonium chloride and 83 g of 1,2-butylene oxide, and the temperature was raised to 90° C. over a period of an hour. After 4 hours of reaction at this temperature, the system was cooled to 60° C., the excess butylene oxide was removed under reduced pressure, and upon cooling a crude product precipitated. This was recrystallized in methanol to obtain the desired 2-[2'-hydroxy-4'-(2"-hydroxy) butoxyphenyl]-5-chlorobenzotriazole in an amount of 110 g. This represented an 86% yield. The melting point of the product was 121° C., and $^1$H-NMR and IR both confirmed the identity of the desired compound.

EXAMPLE 2

Into a 1000 ml autoclave were charged 400 g of isopropyl alcohol, 100 g of 2-(2',4'-dihydroxyphenyl)-5-chlorobenzotriazole, 0.5 g of tetramethylammonium chloride and 138 g of styrene oxide, and the temperature was raised to 110° C. over a period of an hour. After 6 hours of reaction at this temperature, the system was cooled to 60° C., the excess styrene oxide was removed under reduced pressure, and upon cooling a crude product precipitated. This was recrystallized in isopropanol to obtain the desired 2-[2'-hydroxy, 4'-(2"-hydroxy-2"-phenylethoxy)phenyl]-5-chlorobenzotriazole in an amount of 124 g. This represented an 85% yield. The melting point of the product was 137° C., and $^1$H-NMR and IR both confirmed the identity of the desired compound.

EXAMPLE 3

The same procedure as in Example 1 was followed using ethylene oxide as the epoxy compound, to obtain 2-[2'-hydroxy, 4'-(2"-hydroxy)ethoxyphenyl]-5-chlorobenzotriazole at a 90% yield. The melting point of the compound was 147° C.

EXAMPLE 4

The same procedure as in Example 1 was followed using propylene oxide as the epoxy compound, to obtain 2-[2'-hydroxy, 4'-(2"-hydroxy)propoxyphenyl]-5-chlorobenzotriazole at an 80% yield. The melting point of the compound was 147° C.

Comparative Example 1

The same procedure as in Example 1 was followed using 2-(2',4'-dihydroxyphenyl)-benzotriazole, and ethylene oxide as the epoxy compound, to obtain 2-[2'-hydroxy, 4'-(2"- hydroxy)ethoxyphenyl]-benzotriazole at an 89% yield. The melting point of the compound was 160° C.

Comparative Example 2

The same procedure as in Example 1 was followed using 2-(2',4'-dihydroxyphenyl)-benzotriazole, and propylene oxide as the epoxy compound, to obtain 2-[2'-hydroxy, 4'-(2"-hydroxy)propoxyphenyl]-benzotriazole at a 75% yield. The melting point of the compound was 130° C.

The results of thermogravimetric analysis of the compounds of Examples 1–4 and Comparative Examples 1–2 are shown in Table 1. The analysis was performed by raising the temperature by 5° C./min in air, holding the temperature at 210° C. for 30 minutes, and measuring the weight loss (%). The same measurement was made under the same conditions for the compounds of Comparative Examples 3–5 (commercially available products) shown below. The corresponding results are also shown in Table 1.

Comparative Example 3

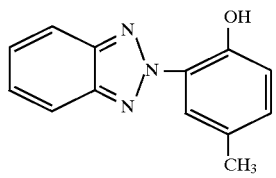

Comparative Example 4

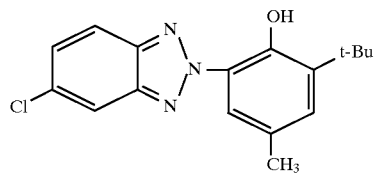

Comparative Example 5

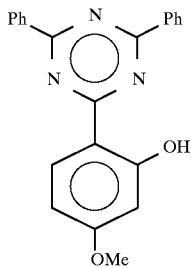

TABLE 1

|  | Color shade | Melting point (°C.) | Weight loss (%) |
| --- | --- | --- | --- |
| Example 1 | light yellow | 121 | 1.8 |
| Example 2 | white | 137 | 0.9 |
| Example 3 | white | 147 | 2.2 |
| Example 4 | light yellow | 147 | 1.9 |
| Comp. Example 1 | white | 160 | 4.6 |
| Comp. Example 2 | light yellow | 130 | 6.2 |
| Comp. Example 3 | light yellow | 128 | 30.4 |

TABLE 1-continued

|  | Color shade | Melting point (°C.) | Weight loss (%) |
| --- | --- | --- | --- |
| Comp. Example 4 | light yellow | 141 | 14.3 |
| Comp. Example 5 | yellow | 205 | 2.3 |

All of the compounds of Examples 1–4 had low thermal weight loss, and excellent sublimation resistance and thermal resistance.

Application Examples

Preparation of aqueous dispersion

Mixtures of 150 g each of the compounds of Examples 1–4 and Comparative Examples 1–5 with 100 g of Lipotol B-12 (anionic surfactant, product of Nikka Chemical Co., Ltd.) and 250 g of water were treated for 4 hours with a sand grinder manufactured by Igarashi Kikai Seizo, KK., to obtain fine aqueous dispersions with an average particle size of 0.40 µm. The particle sizes were measured with a SALD-1100 particle size distribution measuring apparatus manufactured by Shimazu Seisakusho, KK.

Performance Test 1

Each of the aqueous dispersions obtained above were evaluated as to their performance when used to treat fiber materials.

a) Test fabrics

A car seat raised polyester fabric (weight: 650 g/m$^2$) (test fabric 1) and a regular polyester/cation-dyeable polyester (50/50) crossknit fabric (test fabric 2) were treated according to the method described below, and then used for a color fastness to a light test and an adsorption test.

b) Treatment method

A Minicolor dyeing machine manufactured by Techsam Giken (KK.) was used under the conditions listed below for 30 minutes of treatment at 130° C. and 30 minutes of reduction cleaning at 80° C. followed by drying to obtain a grey dyed fabric. This was then subjected to dry heat treatment for 2 minutes at 160° C. using a pin tenter manufactured by Ueno Santekko, KK.

Treatment bath composition

Sumitomo Chemical disperse dye Red-GF 0.6% o.w.f.
Sumitomo Chemical disperse dye Yellow-GF 0.8% o.w.f.
Sumitomo Chemical disperse dye Blue-GF 1.6% o.w.f.
Nikka Sunsalt SD-07 (Nikka Chemical disperse level dyeing agent) 0.5 g/l
90% acetic acid 0.5 g/l
Fine particle aqueous dispersion 2.0% o.w.f.
Liquor ratio 1:20
Reduction cleaning bath composition Sunmol RC-1 (Nikka Chemical soaping agent) 2.0 g/l c) Method of evaluation
(1) Color fastness to light
Method A A high-temperature fade-o-meter (product of Suga Shikenki, KK.) was used for 400 hours of irradiation at 83° C. (1 cm polyurethane backing). The degree of color change was then judged as a series based on a color change grey scale (JIS-L-0804) (with a larger series indicating better color fastness to light).

Method B p A xenon fade-o-meter (product of Suga Shikenki, KK.) was operated for 50 cycles, one cycle consisting of 4.8 hours of irradiation at 89° C. followed by 1 hour of darkness at 38° C. (cumulative irradiance: 105,000 KJ/m², 1 cm polyurethane backing). The degree of color change was then judged as a series based on a color change grey scale (JIS-L-0804) (with a larger series indicating better color fastness to light).

The results are listed in Tables 2 and 3.

TABLE 2

|  | Color fastness to light (test fabric 1) | |
| --- | --- | --- |
|  | Method A | Method B |
| No fine particle aqueous dispersion added | 2 | 2 |
| Fine particle aqueous dispersion: Example 1 | 3–4 | 3–4 |
| Fine particle aqueous dispersion: Example 2 | 3–4 | 3–4 |
| Fine particle aqueous dispersion: Example 3 | 4 | 4 |
| Fine particle aqueous dispersion: Example 4 | 3–4 | 3–4 |
| Fine particle aqueous dispersion: Comp. Example 1 | 3 | 3 |
| Fine particle aqueous dispersion: Comp. Example 2 | 3 | 2–3 |
| Fine particle aqueous dispersion: Comp. Example 3 | 3 | 3 |
| Fine particle aqueous dispersion: Comp. Example 4 | 3–4 | 3–4 |
| Fine particle aqueous dispersion: Comp. Example 5 | 3–4 | 3 |

TABLE 3

|  | Color fastness to light (test fabric 2) | | | |
| --- | --- | --- | --- | --- |
|  | Method A | | Method B | |
|  | Regular portion | Cation dyeable portion | Regular portion | Cation dyeable portion |
| No fine particle aqueous dispersion added | 2 | 2 | 2 | 2 |
| Fine particle aqueous dispersion: Example 1 | 3–4 | 3–4 | 3–4 | 3–4 |
| Fine particle aqueous dispersion: Example 2 | 3–4 | 3–4 | 3–4 | 3–4 |
| Fine particle aqueous dispersion: Example 3 | 4 | 4 | 4 | 4 |
| Fine particle aqueous dispersion: Example 4 | 3–4 | 3–4 | 3–4 | 3–4 |
| Fine particle aqueous dispersion: Comp. Example 1 | 3 | 3 | 3 | 3 |
| Fine particle aqueous dispersion: Comp. Example 2 | 3 | 2–3 | 3 | 3 |
| Fine particle aqueous dispersion: Comp. Example 3 | 3 | 3 | 3 | 3 |
| Fine particle aqueous dispersion: Comp. Example 4 | 3–4 | 3–4 | 3–4 | 3 |
| Fine particle aqueous dispersion: Comp. Example 5 | 3–4 | 3 | 3–4 | 3 |

From these results it is clear that the compounds of Examples 1–4 according to the present invention exhibit superior performance in terms of color fastness to light.

(2) Evaluation of adsorption

Each of the treated fabrics was subjected to Soxhlet extraction (3 hours in chloroform) and the amount of the compound adsorbed into the fabric was measured. The adsorption was calculated according to the following equation, based on comparison with the amount of the compound in a dyeing solution prepared in the same manner prior to dyeing.

Adsorption=(amount of compound extracted/amount of compound in treatment solution)×100

The results are given in Table 4.

TABLE 4

|  | Adsorption (%) | |
| --- | --- | --- |
|  | Test fabric 1 | Test fabric 2 |
| No fine particle aqueous dispersion added | — | — |
| Fine particle aqueous dispersion: Example 1 | 93.8 | 93.2 |
| Fine particle aqueous dispersion: Example 2 | 93.9 | 93.5 |
| Fine particle aqueous dispersion: Example 3 | 93.7 | 93.1 |
| Fine particle aqueous dispersion: Example 4 | 93.3 | 93.0 |
| Fine particle aqueous dispersion: Comp Example 1 | 92.8 | 92.6 |
| Fine particle aqueous dispersion: Comp Example 2 | 92.3 | 91.5 |
| Fine particle aqueous dispersion: Comp Example 3 | 89.6 | 89.0 |
| Fine particle aqueous dispersion: Comp. Example 4 | 87.0 | 88.5 |
| Fine particle aqueous dispersion: Comp. Example 5 | 91.2 | 76.8 |

(3) Evaluation of dry heat sublimation

Each of the treated fabrics was subjected to Soxhlet extraction (3 hours in chloroform) before and after dry heating, and calculation was made of the residue rate of the compound after dry heating and the amount of compound adsorbed onto the fibers after thermal treatment as the final adsorption.

Residue rate=(amount adsorbed after dry heating/amount adsorbed before dry heating)×100

The results are given in Table 5.

TABLE 5

|  | Residue rate after dry heating (%) | |
| --- | --- | --- |
|  | Test fabric 1 | Test fabric 2 |
| No fine particle aqueous dispersion added | — | — |
| Fine particle aqueous dispersion: Example 1 | 96.8 | 96.5 |
| Fine particle aqueous dispersion: Example 2 | 97.9 | 97.8 |
| Fine particle aqueous dispersion: Example 3 | 96.7 | 97.1 |
| Fine particle aqueous dispersion: Example 4 | 96.3 | 96.0 |
| Fine particle aqueous dispersion: Comp. Example 1 | 94.8 | 95.1 |
| Fine particle aqueous dispersion: Comp. Example 2 | 95.3 | 94.8 |
| Fine particle aqueous dispersion: Comp. Example 3 | 56.8 | 55.2 |
| Fine particle aqueous dispersion: Comp. Example 4 | 72.8 | 71.2 |
| Fine particle aqueous dispersion: Comp. Example 5 | 96.2 | 95.4 |

As mentioned above, the ultraviolet absorber of the present invention is capable of imparting excellent color fastness to light and resistance to sublimation when applied to dyed fiber materials, and particularly dyed polyester fiber materials.

What is claimed are:

1. A method of improving a light fastness to ultraviolet light of a synthetic fiber material comprising applying a benzotriazole compound represented by the following general formula (I)

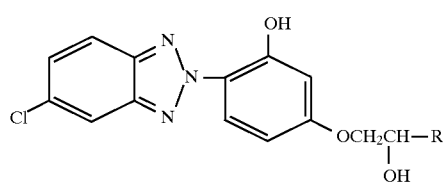

wherein R represents hydrogen, methyl, ethyl or phenyl, to the synthetic fiber material by post-treatment.

2. The method according to claim 1, wherein R is hydrogen.

3. The method according to claim 1, wherein the synthetic fiber material is a cation-dyable polyester fiber-material.

4. The method according to claim 1, wherein the synthetic fiber material is a polyester fiber material.

5. The method according to claim 4, wherein the synthetic fiber material is a cation-dyable polyester fiber-material.

6. The method according to claim 1, wherein the synthetic fiber material is a composite material comprising a polyester fiber material and a fiber material selected from the group consisting of cotton, rayon, wool, nylon, acetate and combinations thereof.

7. A method of post-treating a synthetic fiber material for improved light fastness by absorbing ultraviolet light comprising adsorbing onto the synthetic fiber a benzotriazole compound represented by the following general formula (I)

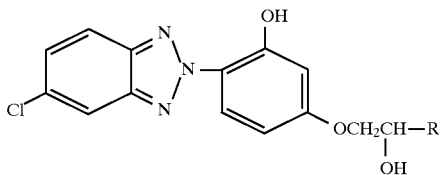

wherein R represents hydrogen, methyl, ethyl or phenyl, in an amount of 0.01% to 10% by weight of the synthetic fiber.

8. The method of claim 7, wherein the amount of benzotriazole compound adsorbed onto the synthetic fiber is 0.1% to 5% by weight of the synthetic fiber.

9. The method of claim 7, wherein R is hydrogen.

10. The method according to claim 7, wherein the synthetic fiber material is a cation-dyable polyester fiber-material.

11. The method of claim 7, wherein the synthetic fiber material is a polyester fiber material.

12. The method of claim 7, wherein the synthetic fiber material is a composite material comprising a polyester fiber material and a fiber material selected from the group consisting of cotton, rayon, wool, nylon, acetate and combinations thereof.

13. A method for improving the light fastness of a synthetic fiber material comprising applying at least two benzotriazole compounds represented by the following general formula (I)

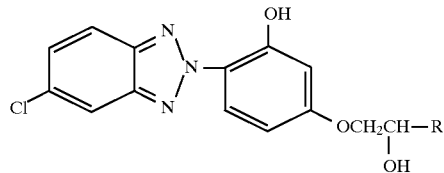

wherein R represents hydrogen, methyl, ethyl or phenyl, to the synthetic fiber material by post treatment.

14. The method of claim 13, wherein R is hydrogen.

15. The method of claim 13, wherein the synthetic fiber material is a polyester fiber material.

16. The method according to claim 13, wherein the synthetic fiber material is a cation-dyable polyester fiber-material.

17. The method of claim 13, wherein the synthetic fiber material is a composite material comprising a polyester fiber material and a fiber material selected from the group consisting of cotton, rayon, wool, nylon, acetate and combinations thereof.

18. The method of claim 13, wherein the benzotriazole compounds are adsorbed onto the synthetic fiber.

19. The method of claim 18 wherein the benzotriazole compounds adsorbed are in the amount of 0.01% to 10% by weight of the synthetic fiber.

20. The method of claim 19, wherein the amount of benzotriazole compounds is from 0.1% to 5% by weight of the synthetic fiber.

* * * * *